United States Patent

Podszun et al.

[11] Patent Number: 5,921,779
[45] Date of Patent: Jul. 13, 1999

[54] DENTAL ADHESIVES

[75] Inventors: Wolfgang Podszun, Köln; Werner Finger, Neuss; Ludger Heiliger, Leverkusen, all of Germany

[73] Assignee: Heraeus Kulzer GmbH & Co. KG, Hanau, Germany

[21] Appl. No.: 08/747,580

[22] Filed: Nov. 13, 1996

[30] Foreign Application Priority Data

Nov. 30, 1995 [DE] Germany ............. 195 44 673

[51] Int. Cl.$^6$ .................. A61C 5/00; A61C 5/04
[52] U.S. Cl. ............ 433/226; 433/228.1; 526/304
[58] Field of Search ............... 433/226, 228.1; 526/304

[56] References Cited

U.S. PATENT DOCUMENTS

| | | |
|---|---|---|
| 4,323,696 | 4/1982 | Schmitz-Josten et al. . |
| 4,437,836 | 3/1984 | Schmitz-Josten et al. . |
| 4,879,402 | 11/1989 | Reiners et al. . |
| 4,952,614 | 8/1990 | Reiners et al. ............. 523/115 |
| 5,204,383 | 4/1993 | Manabe et al. . |
| 5,354,827 | 10/1994 | Müller et al. . |
| 5,362,769 | 11/1994 | Waller et al. . |
| 5,380,772 | 1/1995 | Hasegawa et al. ............. 522/114 |
| 5,519,071 | 5/1996 | Rheinberger et al. . |

FOREIGN PATENT DOCUMENTS

| | | |
|---|---|---|
| 0 023 686 | 2/1981 | European Pat. Off. . |
| 0 254 950 B1 | 2/1988 | European Pat. Off. . |
| 0 305 083 A2 | 3/1989 | European Pat. Off. . |
| 0 361 033 B1 | 4/1990 | European Pat. Off. . |
| 0 546 648 A1 | 6/1993 | European Pat. Off. . |
| 0 554 890 A1 | 8/1993 | European Pat. Off. . |
| 0 661 034 A1 | 7/1995 | European Pat. Off. . |
| 31 35 113 A1 | 3/1983 | Germany . |
| 37 03 080 A1 | 1/1988 | Germany . |
| 37 03 120 A1 | 1/1988 | Germany . |
| 37 03 130 A1 | 1/1988 | Germany . |
| 38 28 170 A1 | 2/1990 | Germany . |
| 41 05 550 A1 | 8/1992 | Germany . |
| WO 93/12760 A1 | 7/1993 | WIPO . |

*Primary Examiner*—Nicholas D. Lucchesi
*Attorney, Agent, or Firm*—Frishauf, Holtz, Goodman, Langer & Chick, P.C.

[57] ABSTRACT

A formulation for use as a dental adhesive in the treatment of the hard tooth substance, to provide enhanced bonding between dental restoration material and the enamel and dentine of the tooth. The formulation contains glycerol di(meth)acrylate, volatile solvent, photo-initiator and, optionally, usual additives and fillers.

14 Claims, No Drawings

DENTAL ADHESIVES

BACKGROUND OF THE INVENTION

1. Field of the Invention

The invention relates to a formulation for use as an adhesive component in the treatment of the hard substance of the tooth. In particular, the invention relates to an adhesive component which can be used for the treatment of enamel and dentine in connection with tooth restoration materials.

Tooth hard substance is built up from tooth enamel and dentine, which differ greatly in their composition. Tooth enamel is built up largely on a mineral basis, in particular from hydroxyapatite. Dentine, in contrast, consists to a considerable proportion, of organic units, such as collagen and other proteins, and contains more water. A specific serious problem in the field of conservative dentistry is to form a durable gap free bond of resin based curable dental filling materials normally used in dentistry, with the hard substance of the tooth (dentine and tooth enamel).

2. Description of Related Art

In the dental field, curable materials are used as dental filling materials. As curable materials, acrylic resin based filling materials, which can be cured by radical polymerization, are generally preferred. A disadvantage of these materials is in their shrinking during the curing process, thus contributing to the formation of gaps. Resin based dental fillings have the additional disadvantage that their adhesion to dentine is poor.

In order to improve bonding with the hard substance of the tooth, so called dental adhesives or bonding agents are used. In this context, dental adhesives are preferred which not only produce good adhesive values with respect to the dentine but also with respect to the enamel. Generally, it is expected that, to obtain an effective formulation, a plurality of components must be used. Thus, for example, in DE-A-38 28 170 and EP-B-0 361 033, a coating substance for collagen-containing materials is described, which consists of
  a) aldehyde
  b) a water-soluble monomer with active hydrogen,
  c) a water-insoluble monomer with two or more polymerizable double bonds,
  d) a photo-initiator,
  e) water,
  f) a solubility agent and/or dispersant and
  g) known additives.

In U.S. Pat. No. 5,354,827 (and DE-A-41 05 550) dental adhesive formulation consisting of
  a) (meth)acrylic acid esters containing formamide groups,
  b) (meth)acrylic esters which can form cross-linkings,
  c) solvents,
  d) optionally other additives,
  e) acids and,
  f) optionally a dispersant
is described. These are the type of dental adhesives over which the present invention provides an improved formulation.

SUMMARY OF THE INVENTION

A formulation has now been discovered which contains only a few components, is easy to use and enables very high adhesive values with respect to both enamel and dentine. The formulation is for use as a dental adhesive in the treatment of the hard tooth substance, to provide enhanced bonding between the dental restoration materials and the enamel and dentine of the tooth. The formulation contains glycerol di(meth)acrylate, volatile solvent, photo-initiator and, optionally, usual additives and fillers.

DESCRIPTION OF THE PREFERRED EMBODIMENT

The formulation according to the invention contains
  a) 20–75% by weight of glycerol di(meth)acrylate,
  b) 20–75% by weight of a volatile solvent miscible with water,
  c) 0.01–2.5% by weight of a photo-initiator and optionally
  d) 0–40% by weight of generally known additives and fillers.

The term "glycerol di(meth)acrylate" in the context of the present invention means diesters of 1 mole of glycerol with two moles acrylic acid or methacrylic acid or mixtures thereof. As examples, the following compounds are noted:

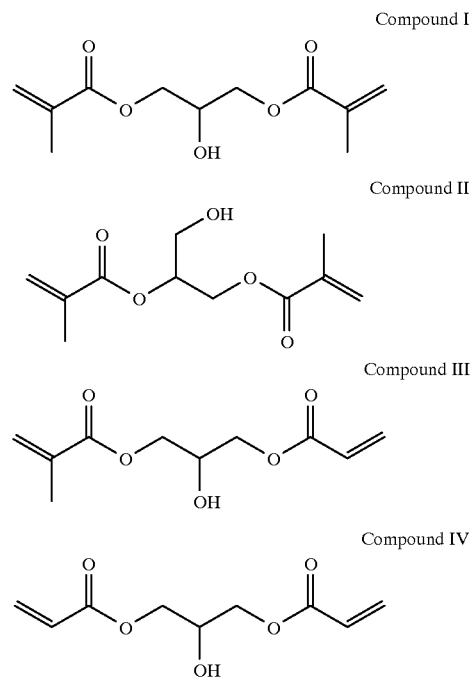

Mixtures of different glycerol di(meth)acrylates, including, in particular, isomeric mixtures of 1,2-glycerol di(meth)acrylates and 1,3-glycerol di(meth)acrylates, can be used in the present invention formulation.

Volatile solvents miscible with water are primarily those with a vapor pressure at a minimum of 100 torr at ambient temperature. Aliphatic alcohols with one to four carbon atoms, acetone, 1,4-dioxane and tetrahydrofuran are preferred. Acetone and ethyl alcohol are particularly preferred.

In the context of the present invention, photo-initiators form free radicals which initiate radical polymerization when irradiated with light, for example, UV light, visible light or laser light.

These initiators for photo polymerization are generally known from the literature, e.g. U.S. Pat. No. 5,354,827 and U.S. Pat. No. 4,437,836, for example. Preferably, they are mono- or dicarbonyl compounds such as benzophenone; benzoin and its derivatives, in particular benzoin methyl ether; benzil and benzil derivatives; other dicarbonyl compounds, such as diacetyl, 2,3-pentanedione and α-diketo derivatives of norbornane and substituted norbornanes; metal carbonyls, such as pentacarbonyl manganese; or quinones, such as 9,10-phenanthrenequinone and naphthoquinone. Especially preferred is camphorquinone.

The formulation according to the invention generally contains 0.01 to 2.5% by weight, preferably 0.1 to 0.5% by weight, of a photo-initiator, with respect to the total weight of the formulation.

It can be advantageous to add co-activators (or "accelerators") to the formulation according to the invention, which accelerate the photo polymerization reaction. These are also well known in the art (e.g. UK 1 408 265, U.S. Pat. No. 5,354,827 and U.S. Pat. No. 4,437,836). Known co-activators are, for example, amines, such as p-toluidine and dimethyl-p-toluidine, trialkylamines, such as trihexylamine, polyamines, such as N,N,N',N'-tetraalkylenediamines, barbituric acid and dialkyl barbituric acids. Dimethylamino benzene-sulphonamides as described in DE-A- 31 35 113 or U.S. Pat. No. 4,437,836 are particularly preferred.

Co-activators are generally used in a quantity of 0.02 to 4% by weight, preferably 0.2 to 1% by weight, with respect to the total weight of the formulation.

In addition to the glycerol di(meth)acrylate, solvent, photo-initiator and co-activator, the formulation according to the invention can, if applicable, contain additional (meth) acrylic acid esters as co-monomers. In particular are esters of (meth)acrylic acid with mono- to pentahydric alcohols with 2 to 30 carbon atoms. Epoxide (meth)acrylates and urethane (meth)acrylates are particularly preferred.

Also found useful are tricyclodecane derivatives (EP-A-0 023 686 or U.S. Pat. No. 4,323,696) and reaction products from polyols, diisocyanates and hydroxyalkyl methacrylates (DE-A-37 03 120 or U.S. Pat. No. 4,952,614, DE-A-37 03 080 or EP B-0 254 950 and DE-A-37 03 130 or U.S. Pat. No. 4,879,402).

Particularly preferred as (meth)acrylic acid ester is so-called Bis-GMA with the formula

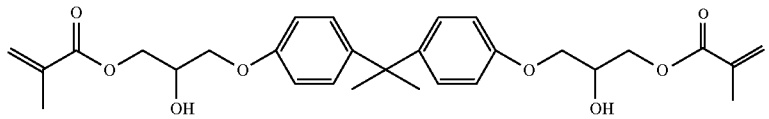

Of course, it is possible to use mixtures of the various (meth)acrylic acid esters. For example, mixtures of 20–70 parts by weight of Bis-GMA and 30–80 parts by weight of triethylene glycol di(meth)acrylate are noted.

It is possible to obtain a particularly good elasticity in a layer made of the formulation and cured by means of photo polymerization with a formulation which contains polyethylene glycol di(meth)acrylates, in particular, polyethylene glycol di(meth)acrylates with a molecular weight of 200–2000.

It has also been found that the generally very high adhesive values with respect to dentine can be further increased by using a fine particle sized inorganic filler. Suitable dental fillers are, for example, quartz, cristobalite, vitreous silica, highly dispersed silica, alumina and glass-ceramics. The mean particle size of the inorganic fillers is generally in the range of 5–2000 nm, preferably in the range of 10–100 nm. Particularly suitable inorganic fillers are highly dispersed silicas, which, for example, can be produced by flame hydrolysis.

A preferred formulation according to the invention is characterized by the following composition:

a) 20–70% by weight of glycerol di(meth)acrylate,
b) 20–70% by weight of a volatile solvent miscible with water,
c) 0.01–2.5% by weight of a photo-initiator,
d1) 5–20% by weight of a filler and, optionally,
d2) 0–25% by weight of generally known additives.

Preferably, the fillers are pretreated, for example, with silanization agents consisting of organosilane compounds (Progress in Organic Coatings 11, 297–308 (1983)). A preferred silanization agent is 3-methacryloyloxypropyl-trimethoxysilane.

The formulation according to the invention can furthermore contain generally known or standard dental additives such as stabilizers, inhibitors and light stabilisers.

The formulation according to the invention can be produced in a simple manner by mixing the individual components. It is used as an adhesive component for treating the hard substance of the tooth. It greatly improves the adhesion between the hard substance of the tooth and the dental restoration.

In a special embodiment, prior to treatment with the formulation according to the invention, the hard substance of the tooth is conditioned with a conditioning fluid which has a pH value in the range of 0.1 to 3.5. This conditioning fluid generally contains acids with a $pK_a$ value less then 5 and, if applicable, an amphoteric amino compound with a $pK_a$ value in the range of 9.0 to 10.6 and a $PK_b$ value in the range of 11.5 to 12.5. The following acids, for example, can be used in the conditioning fluid: phosphoric acid, nitric acid, pyruvic acid, citric acid, oxalic acid, ethylenediaminetetraacetic acid, acetic acid, tartaric acid, malic acid. Furthermore, the conditioning fluid can contain polyethylene glycols and/or metal hydroxides. In particular, the above listed polybasic acids can partially also be in the form of metallic salts, as long as free acid functions remain. Treatment with a dilute phosphoric acid is preferred. Suitable concentrations of phosphoric acid are 10–60% by weight, preferably 20–40% by weight. The conditioning fluid may also contain thickening agents, for example, fine sized silica, to obtain a fluid with suitable consistency for use on the tooth.

Use of the formulation according to the invention can, for example, be carried out as follows:

When performing dental restoration, after mechanically cleaning the tooth surface, one applies the conditioning fluid to the tooth surface, allows it to act for a short period of time (for example, 60 seconds), rinses the tooth surface with water and dries it. Thereafter, one applies the formulation according to the invention in one or several layers with, for example, a small brush, dries it with an air flow and irradiates it with a commercially available polymerization lamp. Subsequently, the dental filling material is applied, for example, a polymerizable filling material standard in the dental field.

In the following, for purposes of a more detailed explanation, several examples (example 1–4) of the formulation according to the invention are listed and a test of their effectiveness by determining the shear bonding strenghts of dental fillings on dentine and enamel pretreated therewith (Example 5) is described.

EXAMPLE 1A–D

The following formulations are produced by intensive mixing the components together.

| Example 1 | A | | B | | C | | D | |
|---|---|---|---|---|---|---|---|---|
| Glycerol dimethacrylate (Compound I) | 10.0 | g | 7.5 | g | 5.0 | g | 2.5 | g |
| Acetone | — | | 2.5 | g | 5.0 | g | 7.5 | g |
| Camphor quinone | 20 | mg | 20 | mg | 20 | mg | 20 | mg |
| Diallyl sulphonamide* | 50 | mg | 50 | mg | 50 | mg | 50 | mg |

Example 1A is outside of the invention.

EXAMPLE 2

The following formulation is produced by intensive mixing the components together.

| | | |
|---|---|---|
| Glycerol acrylatemethacrylate (Compound III) | 5.0 | g |
| Acetone | 5.0 | g |
| Camphor quinone | 20 | mg |
| Diallyl sulphonamide* | 50 | mg |

EXAMPLE 3A–C

The following formulations are produced by intensive mixing the components together.

| Example 3 | A | | B | | C | |
|---|---|---|---|---|---|---|
| Glycerol dimethacrylate (Compound I) | 7.5 | g | 5.0 | g | 2.5 | g |
| Ethanol | 2.5 | g | 5.0 | g | 7.5 | g |
| Camphor quinone | 20 | mg | 20 | mg | 20 | mg |
| Diallyl sulphonamide* | 50 | mg | 50 | mg | 50 | mg |

EXAMPLE 4A–D

The following formulations are produced by intensive mixing the components together.

| Example 4 | A | B | C | D |
|---|---|---|---|---|
| Glycerol dimethacrylate (Compound I) | 5.0 g | 5.0 g | 5.0 g | 5.0 g |
| Acetone | 5.0 g | 5.0 g | 5.0 g | 5.0 g |
| Silanized silica** | 0.5 g | 1.0 g | 2.0 g | 3.0 g |
| Camphor quinone | 20 mg | 20 mg | 20 mg | 20 mg |
| Diallyl sulphonamide* | 50 mg | 50 mg | 50 mg | 50 mg |

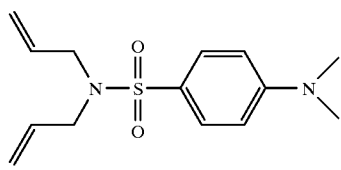

**Highly dispersed silica with a BET surface of 200 m$^2$/g and a mean particle size of 14 nm, silanized with γ-methacryloyloxypropyltrimethoxysilane

EXAMPLE 5

Determination of shear bonding strength to dentine

The effectiveness of the formulations described in examples 1–4 as dental adhesives is tested by determining the shear bonding strength to dentine. Human teeth are used which had been preserved in 1% chloramine solution for a maximum of three months after their extraction. Prior to their use in the bonding test and after a careful cleaning under running water, the teeth were stored in a physiological salt solution for a minimum of three but a maximum of ten days. On the day before their use in the bonding test, the teeth, lying on an approximal side, are individually embedded with epoxy resin (LEKUTHERM® X20, curing agent T3) in cylindrical rubber molds having a diameter of 25 mm and a height of 12 mm. The teeth were ground by means of wet grinding with SiC papers with coarseness of 240, 320, 400 and, finally, 600, to the extent that a sufficiently large enamel-close dentin surface is freed to allow bonding to it synthetic cylinder with a diameter of 3.5 mm. Subsequent to rinsing with de-ionized water and drying with an air flow, the conditioning agent GLUMA® CPS gel (20% $H_3PO_4$, Bayer) is applied in a circular motion for 30 seconds using an absorbent cotton pellet, carefully rinsed with water and, by dabbing with cellucotton, superficially freed from water (wet technique). Three layers of the formulations from examples 1–4 are applied with a brush onto the conditioned dentin surface, dried with a compressed-air flow and irradiated with the TRANSLUX® CL (Kulzer) light device for a duration of 20 seconds. The pretreated test sample is then clamped with a clamping device under a double-part cylindrical teflon mold (diameter of 3.5 mm, height of 1 mm). Then the teflon mold is filled with the resin based filling material PEKAFILL® (U, Bayer AG) by means of a syringe, covered with an $O_2$-impermeable strip and irradiated with the TRANSLUX® CL light device for a duration of 60 seconds. Immediately afterwards, the teflon mold is removed and the cylindrical test sample stored in 37° C. warm water for a period of 24 hours until initiation of the shearing stress. To determine the shear bonding strength, the cylindrical test sample is stressed in a universal testing machine with the aid of a force piece parallel and close to the ground tooth surface, at a speed of 1 mm/minute, until the cylinder separates from the tooth. The shear bonding strength is the quotient of the breaking strength and the bonding surface (i. e. breaking strength per unit of area) and is determined on the basis of 5 test samples each and indicated in the table as their mean value.

Determination of shear bonding strength to enamel

For determination of the shear bonding strenth to enamel treated with the formulations described in examples 1–4, extracted human teeth with intact labial enamel surfaces are embedded in epoxy resin and ground with wet SiC paper with a coarseness of 240 to 600, in order to free a plane, peripheral enamel surface. The conditioning agent, GLUMA® CPS gel, is applied onto the enamel surface and, after 30 seconds, is rinsed off carefully with de-ionized water. The drying is performed only superficially with a weak compressed-air flow, until the treated surface appears chalky white. All other steps are indentical to the ones described previously for determining the shear bonding strength to dentine. The values for the shear bonding strength to enamel are indicated in the table.

| Formulation | Shear bonding strength to dentin | Shear bonding strength to enamel |
|---|---|---|
| Example 1A | 8.2 MPa | 32.7 ± 1.7 MPa |
| Example 1B | 9.5 MPa | 38.3 ± 6.2 MPa |
| Example 1C | 14.5 MPa | 34.7 ± 1.7 MPa |
| Example 1D | 13.5 MPa | 31.7 ± 2.6 MPa |
| Example 2 | 15.8 MPa | 31.8 ± 8.6 MPa |
| Example 3A | 13.5 MPa | 32.2 ± 1.5 MPa |
| Example 3B | 18.6 MPa | 32.5 ± 5.4 MPa |
| Example 3C | 8.7 MPa | 28.5 ± 3.8 MPa |
| Example 4A | 14.7 MPa | 33.6 ± 4.6 MPa |
| Example 4B | 19.0 MPa | 29.5 ± 3.3 MPa |
| Example 4C | 14.5 MPa | 34.0 ± 2.9 MPa |
| Example 4D | 11.0 MPa | 17.9 ± 4.1 MPa |

Example 1A is outside of the invention.

It will be appreciated that the instant specification is set forth by way of illustration and not limitation, and that various modifications and changes may be made without departing from the spirit and scope of the present invention.

What is claimed is:

1. A formulation for use as an adhesive component in the repair of a hard substance of a tooth, said formulation comprising
   a) 20–75% by weight of glycerol di(meth)acrylate,
   b) 20–75% by weight of a volatile solvent miscible with water,
   c) 0.01–2.5% by weight of a photo-initiator, and
   d) 0–40% by weight of dental additives and fillers.

2. A formulation according to claim 1, wherein
   the glycerol di(meth)acrylate is an isomeric mixture of 1,2-glycerol di(meth)acrylate and 1,3-glycerol di(meth)acrylate; and
   the volatile solvent is a $C_1$–$C_4$ aliphatic alcohol, acetone, 1,4 dioxane or tetrahydrofuran.

3. Dental adhesive comprising the formulation according to claim 1.

4. A formulation according to claim 1, wherein said dental additives comprise polyethylene glycol di(meth)acrylates having a molecular weight of 200–2,000.

5. A formulation according to claim 1 consisting of
   a) 20–75% by weight of glycerol di(meth)acrylate,
   b) 20–75% by weight of a volatile solvent miscible with water,
   c) 0.01–2.5% by weight of a photo-initiator, and
   d) 0–40% by weight of polyethylene glycol di(methyl) acrylates having a molecular weight of 200–2,000.

6. A formulation for use as an adhesive component in the repair of the hard substance of a tooth, said formulation comprising
   a) 20–70% by weight of glycerol di(meth)acrylate,
   b) 20–70% by weight of a volatile solvent miscible with water,
   c) 0.01–2.5% by weight of a photo-initiator,
   d1) 5–20% by weight of a filler and,
   d2) 0–25% by weight of dental additives.

7. A formulation according to claim 6, wherein said filler is highly dispersed silica with a mean particle size of 5–2000 nm.

8. A formulation according to claim 7, wherein the mean particle size of the highly dispersed silica is 10–100 nm.

9. A formulation according to claim 6, wherein
   the glycerol di(meth)acrylate is an isomeric mixture of 1,2-glycerol di(meth)acrylate and 1,3-glycerol di(meth)acrylate; and
   the volatile solvent is a $C_1$–$C_4$ aliphatic alcohol, acetone, 1,4 dioxane or tetrahydrofuran.

10. A formulation according to claim 9, wherein said filler is highly dispersed silica with a mean particle size of 5–2000 nm.

11. A formulation according to claim 10, wherein the mean particle size of the highly dispersed silica is 10–100 nm.

12. Dental adhesive comprising the formulation according to claim 6.

13. A formulation according to claim 6, wherein said dental additives comprise polyethylene glycol di(meth) acrylates having a molecular weight of 200–2,000.

14. A formulation according to claim 6 consisting of
   a) 20–70% by weight of glycerol di(meth)acrylate,
   b) 20–70% by weight of a volatile solvent miscible with water,
   c) 0.01–2.5% by weight of a photo-initiator,
   d1) 5–20% by weight of a filler and
   d2) 0–25% by weight of polyethylene glycol di(methyl) acrylates having a molecular weight of 200–2,000.

* * * * *